(12) United States Patent
Keller (10) Patent No.: US 8,591,229 B2
(45) Date of Patent: Nov. 26, 2013

(54) DEVICES AND METHODS FOR CREATING A POSITIVE PRESSURE ENVIRONMENT FOR TREATMENT OF ORAL BIOFILMS ASSOCIATED WITH PERIODONTAL DISEASE

(76) Inventor: Duane C. Keller, St. Louis, MO (US)

( * ) Notice: Subject to any disclaimer, the term of this patent is extended or adjusted under 35 U.S.C. 154(b) by 0 days.

(21) Appl. No.: 13/027,925

(22) Filed: Feb. 15, 2011

(65) Prior Publication Data

US 2012/0156640 A1 Jun. 21, 2012

Related U.S. Application Data

(60) Provisional application No. 61/423,852, filed on Dec. 16, 2010.

(51) Int. Cl.
*A61C 17/00* (2006.01)
(52) U.S. Cl.
USPC ............................................................ 433/80
(58) Field of Classification Search
USPC ........... 433/37, 80, 93, 48; 128/861, 846, 859
See application file for complete search history.

(56) References Cited

U.S. PATENT DOCUMENTS

| | | | |
|---|---|---|---|
| 3,481,329 A * | 12/1969 | Warren, Jr. .................... | 433/141 |
| 4,514,382 A | 4/1985 | Gaffar et al. | |
| 4,560,351 A * | 12/1985 | Osborne ......................... | 433/80 |
| 4,568,535 A | 2/1986 | Loesche | |
| 4,569,837 A | 2/1986 | Suzuki et al. | |
| 4,670,252 A | 6/1987 | Sampathkumar | |
| 4,701,320 A | 10/1987 | Hasegawa et al. | |
| 4,751,051 A | 6/1988 | Thompson et al. | |
| 4,819,158 A | 4/1989 | Miyashita | |
| 4,842,846 A | 6/1989 | Nakano | |
| 4,892,736 A | 1/1990 | Goodson | |
| 4,906,670 A | 3/1990 | Higashi et al. | |
| 4,916,193 A | 4/1990 | Tang et al. | |
| 4,933,182 A | 6/1990 | Higashi et al. | |
| 4,963,347 A | 10/1990 | Humphries et al. | |
| 4,966,774 A | 10/1990 | Nakano et al. | |
| 4,975,271 A | 12/1990 | Dunn et al. | |
| 4,980,152 A | 12/1990 | Frazier et al. | |
| 4,985,235 A | 1/1991 | Kligman | |
| 4,990,329 A | 2/1991 | Sampathkumar | |
| 5,032,384 A | 7/1991 | Yeh et al. | |
| 5,057,497 A | 10/1991 | Calam et al. | |
| 5,087,451 A | 2/1992 | Wilson et al. | |

(Continued)

OTHER PUBLICATIONS

Feres et. al. Antibiotics in the Treatment of Periodontal Diseases: Microbiological Basis and Clinical Applications. Ann Roy Australas Coll Dent Surg, Jun. 2008; 19:37-44; p. 40, col. 2, para 4; p. 41, col. 1, para 1.

(Continued)

*Primary Examiner* — Heidi M Eide
(74) *Attorney, Agent, or Firm* — Polster, Lieder, Woodruff & Lucchesi, LC (57) ABSTRACT

A medicament delivery tray and method for treating periodontal disease include fitting of a tray about the teeth and gums wherein the tray includes a seal that creates a substantially airtight seal against the gumline and a substantially airtight treatment chamber about the enclosed teeth and gums, the tray further having a reinforcing skirt providing a biasing force to the seal wherein a positive pressure can be created in the treatment chamber for forcing a medicament into the gums about the enclosed teeth.

20 Claims, 7 Drawing Sheets

(56) References Cited

U.S. PATENT DOCUMENTS

| | | | |
|---|---|---|---|
| 5,110,583 A | 5/1992 | Sampathkumar |
| 5,129,824 A | 7/1992 | Keller |
| 5,160,737 A | 11/1992 | Friedman et al. |
| 5,176,901 A | 1/1993 | Gallopo et al. |
| 5,188,817 A | 2/1993 | Ozick |
| 5,217,710 A | 6/1993 | Williams et al. |
| 5,240,710 A | 8/1993 | Bar-Shalom et al. |
| 5,277,908 A | 1/1994 | Beckman et al. |
| 5,330,357 A | 7/1994 | Keller |
| 5,340,566 A | 8/1994 | Curtis et al. |
| 5,372,802 A | 12/1994 | Barrows et al. |
| 5,374,418 A | 12/1994 | Oshino et al. |
| 5,409,703 A | 4/1995 | McAnalley et al. |
| 5,419,703 A | 5/1995 | Warrin et al. |
| 5,438,076 A | 8/1995 | Friedman et al. |
| 5,472,684 A | 12/1995 | Nabi et al. |
| 5,599,553 A | 2/1997 | Chung |
| 5,605,676 A | 2/1997 | Gaffar et al. |
| 5,607,681 A | 3/1997 | Galley et al. |
| 5,607,686 A | 3/1997 | Totakura et al. |
| 5,616,313 A | 4/1997 | Williams et al. |
| 5,632,972 A | 5/1997 | Williams et al. |
| 5,639,795 A | 6/1997 | Friedman et al. |
| 5,648,399 A | 7/1997 | Friedman et al. |
| 5,701,320 A | 12/1997 | Sugiyama et al. |
| 5,709,873 A | 1/1998 | Bar-Shalom et al. |
| 5,730,995 A | 3/1998 | Shirono et al. |
| 5,800,803 A | 9/1998 | Mirajkar et al. |
| 5,817,294 A | 10/1998 | Arnold |
| 5,820,841 A | 10/1998 | Chen et al. |
| 5,827,503 A | 10/1998 | Schwabe |
| 5,885,553 A | 3/1999 | Michael |
| 5,906,811 A | 5/1999 | Hersh |
| 5,908,613 A | 6/1999 | Bozzacco |
| 5,908,614 A | 6/1999 | Montgomery |
| 5,928,187 A | 7/1999 | Glukhov et al. |
| 5,939,080 A | 8/1999 | Michael et al. |
| 5,998,487 A | 12/1999 | Brahms et al. |
| 6,049,002 A | 4/2000 | Mattila et al. |
| 6,080,712 A | 6/2000 | Revell et al. |
| 6,153,210 A | 11/2000 | Roberts et al. |
| 6,200,550 B1 | 3/2001 | Masterson et al. |
| 6,228,347 B1 | 5/2001 | Hersh |
| 6,228,354 B1 | 5/2001 | Jeng |
| 6,232,340 B1 | 5/2001 | Zhang et al. |
| 6,247,930 B1 | 6/2001 | Chiang et al. |
| 6,290,934 B1 | 9/2001 | Kramer et al. |
| 6,314,960 B1 | 11/2001 | Vines |
| 6,325,991 B1 | 12/2001 | Draheim |
| 6,409,992 B1 | 6/2002 | Kleinberg et al. |
| 6,416,745 B1 | 7/2002 | Markowitz et al. |
| 6,610,274 B1 | 8/2003 | Gardner |
| 6,682,722 B2 | 1/2004 | Majeti et al. |
| 6,685,921 B2 | 2/2004 | Lawlor |
| 6,692,727 B1 | 2/2004 | Yue et al. |
| 6,764,690 B2 | 7/2004 | Ahola et al. |
| 6,776,979 B2 | 8/2004 | Frager et al. |
| 6,929,790 B2 | 8/2005 | Kleinberg et al. |
| 7,018,622 B2 | 3/2006 | Goodhart et al. |
| 7,025,950 B2 | 4/2006 | Majeti et al. |
| 7,094,431 B2 | 8/2006 | Peshoff |
| 7,150,884 B1 | 12/2006 | Hilgren et al. |
| 7,190,884 B2 | 3/2007 | Fujiwara et al. |
| 2001/0038997 A1* | 11/2001 | Lindquist ............... 433/215 |
| 2002/0110780 A1* | 8/2002 | Zegarelli ............... 433/80 |
| 2004/0019110 A1 | 1/2004 | Van Dyke et al. |
| 2004/0091432 A1 | 5/2004 | Dulin |
| 2004/0097432 A1 | 5/2004 | Roh-Schmidt et al. |
| 2004/0126440 A1 | 7/2004 | Frager et al. |
| 2004/0265396 A1 | 12/2004 | Peshoff |
| 2005/0203587 A1 | 9/2005 | Liebergesell |
| 2006/0034782 A1 | 2/2006 | Brown et al. |
| 2006/0036194 A1 | 2/2006 | Schultheiss et al. |
| 2006/0093561 A1 | 5/2006 | Kennedy |
| 2006/0182813 A1 | 8/2006 | Holladay |
| 2006/0257331 A1 | 11/2006 | Dulin |
| 2006/0271148 A1 | 11/2006 | Liebergesell et al. |
| 2007/0122490 A1 | 5/2007 | Peshoff |

OTHER PUBLICATIONS

Kolenbrander et al. Communication among Oral Bacteria. Microbiol. Mol. Biol. Rev. 2002, 66(3): 486-505; p. 486, col. 2, para 3; p. 487, col. 1 para 1; p. 488, col. 2, para 1; p. 489, col. 1, para 1; p. 497, col. 1, para 1-2.

* cited by examiner

DEVICES AND METHODS FOR CREATING A POSITIVE PRESSURE ENVIRONMENT FOR TREATMENT OF ORAL BIOFILMS ASSOCIATED WITH PERIODONTAL DISEASE

CROSS-REFERENCE TO RELATED APPLICATIONS

This application claims the benefit of U.S. provisional application No. 61/423,852 filed Dec. 16, 2010, which is incorporated herein in its entirety by reference.

BACKGROUND OF THE INVENTION

The present disclosure relates to treatment of oral diseases and, more specifically, to devices and methods for treating oral biofilm composed of microbial components including bacterial, fungal, and viral components that can result in periodontal disease.

The statements in this section merely provide background information related to the present disclosure and may not constitute prior art.

Presently, dental trays are used to deliver selected medications for treating multiple oral conditions including periodontal conditions of the teeth and gums. These trays provide for the application of medicaments in close proximity to the teeth and gums such that the medicaments placed in the chamber of the tray are in contact with the selected tissues and/or infected gums. The trays must be placed on the teeth and gums for a sufficient period of time to maintain the medicaments in their proximity to the oral biofilm within the gums and tissues so that the medications can penetrate the biofilm with an expectation that the proximate positioning of the medicament will make direct contact therewith to begin the modification of the micro-environment. This often requires a number of repeated applications in order to adequately penetrate the biofilm as the proximate position of the medication with the biofilm may not always make the direct contact that is required. Repeated applications of the current proximate positioning trays must be applied to penetrate the biofilm and thereby control the microbial pathogens that cause the inflammatory conditions resulting in an infection in the host.

Current medicament delivery trays do not ensure that the medicament is delivered directly to the biofilm, but only place the medicament in close proximity to where the biofilm should be located. Current methods are not able to therefore adequately modify the localized environment, such as altering the environment from one conducive to disease to one conducive to health and healing and/or the ability to manage and maintain such an environment one established. As such, there is a need for a device and method for ensuring that the medicaments are applied directly to the biofilm to be treated, and that such direct application provides if for an ensured period of time for each use of the device and application of the treatment method.

BRIEF SUMMARY OF THE INVENTION

The inventor hereof has succeeded at designing apparatus and methods for the treatment of biofilm that can be associated with periodontal disease and other infections through the delivery of medicament directly to and about the biofilm under a controlled positive pressure so that the medicaments are delivered and maintained at the biofilm being treated during course of the treatment. As designed by the inventor, the present devices and methods provides application of the medicament under a positive pressure that enhances the control over the medication penetration of the biofilm during treatment. Through use hereof, the chemical and mechanical alterations of the biofilm can be controlled to modifying the biofilm environment from a situation that was favorable to pathogenic conditions to a condition that favors the host health and healing. The modified environment is maintained by regular use of the apparatus and method so the micro-environment of the tissues is conducive to health and healing and makes it difficult for the microorganisms to reestablish a pathogenic environment.

According to one aspect, an apparatus for the treatment of a biofilm associated with periodontal disease including a body configured to be fitted about all of the upper or lower teeth of a patient for enclosing the teeth. The body has an outer wall and an inner wall composed of resilient elastomeric material molded for substantially conforming to enclosed teeth and gum tissue proximate to the teeth. The body including one or more internal recesses defined between the inner wall and the outer wall and configured for receiving the enclosed teeth, and having a top outer surface positioned opposite to the one or more internal recesses and between an external surface of the outer wall and an external surface of the inner wall. A raised seal is formed about an inner surface of the outer wall and an inner surface of the inner wall and surrounding the recesses and corresponding to a location along a gum line of the gum tissue of the patient associated with the enclosed teeth. The raised seal being configured to extend about the gum tissue and spaced apart from the teeth, and configured to form a substantially air tight seal against the gum line. A skirt is positioned external to the outer wall and to the inner wall of the body having the raised seal formed thereon. The skirt reinforces the outer wall and the inner wall and providing increased stiffness and a biasing force thereto and to the raised seal to the gum line after placement of the apparatus onto the gum tissue and about the teeth.

According to another aspect, a dental medicament delivery tray having a body configured to be fitted about all of the upper or lower teeth of a patient for enclosing the teeth. The body of the tray has an outer wall and an inner wall composed of resilient elastomeric material molded for substantially conforming to enclosed teeth and gum tissue proximate to the teeth. The tray also has one or more internal recesses defined between the inner wall and the outer wall configured for receiving the enclosed teeth. The tray also has a top outer surface positioned opposite to the one or more internal recesses and between an external surface of the outer wall and an external surface of the inner wall and a raised seal formed about an inner surface of the outer wall and an inner surface of the inner wall and surrounding the recesses and corresponding to a location along a gum line of the patient associated with the enclosed teeth. The raised seal is configured to extend about the gum and spaced apart from the teeth, and to form a substantially air tight seal against the gum line. The tray includes means for reinforcing the outer and inner walls proximate to the raised seal and restricting an outward movement of the walls of the body during and after placement of the tray onto the gumline for increasing the substantial air tight seal against the gumline.

According to yet another aspect, a method for treating a biofilm associated with periodontal disease includes fitting a tray as described in the above assembly, applying a medicament within the recesses and creating a positive pressure within the recesses after the tray is fitted about the teeth and gums and about the medicament.

According to still another aspect, a method for treating periodontal disease includes fitting a substantially airtight medicament tray defining a treatment cavity or chamber about the teeth and gum tissue of a patient to enclose the teeth and gum tissue. The tray includes a raised seal for engaging a gumline of the gum tissue for forming a substantially airtight treatment chamber about the enclosed teeth and gum tissue. The method also includes inserting a medicament within the treatment chamber and applying a positive pressure to the substantially airtight treatment chamber and about the enclosed teeth and gum tissue.

Further aspects of the present disclosure will be in part apparent and in part pointed out below. It should be understood that various aspects of the disclosure may be implemented individually or in combination with one another. It should also be understood that the detailed description and drawings, while indicating certain exemplary embodiments, are intended for purposes of illustration only and should not be construed as limiting the scope of the disclosure.

BRIEF DESCRIPTION OF THE DRAWINGS

It should be understood that throughout the drawings, corresponding reference numerals indicate like or corresponding parts and features.

DETAILED DESCRIPTION

The following description is merely exemplary in nature and is not intended to limit the present disclosure or the disclosure's applications or uses.

Before turning to the figures and the various exemplary embodiments illustrated therein, a detailed overview of various embodiments and aspects is provided for purposes of breadth of scope, context, clarity, and completeness. As an initial note, any reference herein that refers to an orientation such as upper, lower, inner and outer, is by way of exemplary reference to the drawings. It should be understood to those skilled in the art that the oral tray as described herein can be oriented in a different direction and that such orientation references would then shift, but still be within the scope of the present disclosure.

Figure 1:
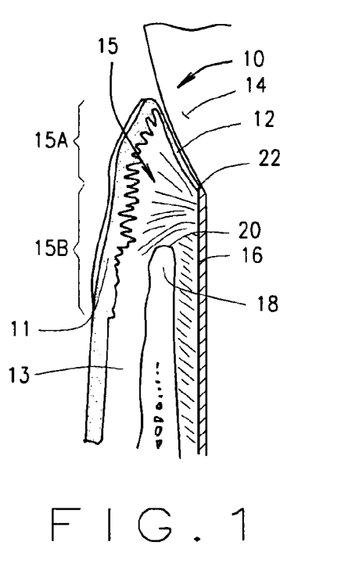
FIG. 1 is a cross-sectional view of a healthy tooth.

FIG. 1 shows a healthy tooth, as generally indicated at 10. It is seen that a healthy tooth has gum tissue 11 with a junctional epithelium 12 covering the enamel 14 of the tooth 10, and attaching to the surface of the tooth 10 so that the cementum 16 of the tooth 10 is not exposed. The periodontal ligament 13 is composed of connective tissue fibers that anchor the tooth 10 with one end of each fiber being attached to the cementum 16 covering the root of the tooth 10 and the other end being embedded in the bony tooth socket defined by the aveolar bone 18. The aveolar bone 18 has an aveolar crest 20 extending nearly to the cementoenamel junction 22 to form the bony tooth socket for the tooth 10. The upper region of gum tissue includes the regions having the junctional epithelium 12 and the cementoenamel junction 22 (CEJ) are referred to as gingiva 15 that includes the marginal gingiva 15A, and the low region of gum tissue below the cementoenamel junction 22 is referred to as the attached gingiva 15B referring as the portion where, in a healthy tooth, the gum tissue 11 is attached to the cementum 16.

Figure 2:
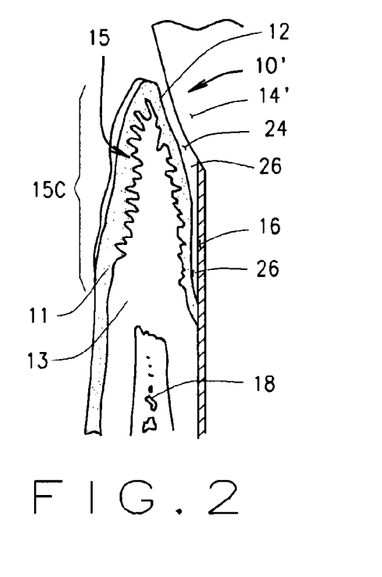
FIG. 2 is a cross-sectional view of a tooth with periodontal disease showing keratinized gingiva partially separated from the tooth.
Figure 3:
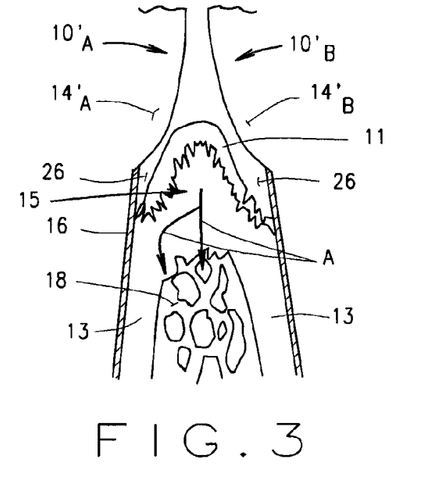
FIGS. 3 and 4 are cross-sectional views of a tooth showing the progression of periodontal disease and the deterioration of the aveolar crest.
Figure 4:
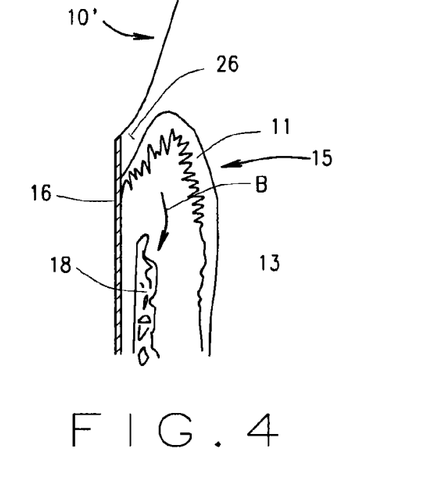

By comparison, a diseased tooth 10' with enamel 14' and cement enamel junction (CEJ) 15(C), as shown in FIGS. 2, 3 and 4, has inflammation from one or more biofilm (not shown) that has caused periodontal disease. In the diseased tooth 10' the junctional epithelium 12 is moved apically (or toward the apex of the root) thereby exposing the cementum 16 and enlarging a sulcus 24 between the gum tissue 11 and the tooth 10' creating a pocket 26 therebetween. As the inflammation spreads, the aveolar bone 18 is destroyed, such as shown as a reduction in height in FIG. 2. This reduction in aveolar bone 18 and the creation of pocket 16 increases tooth mobility and can lead to a loss of the tooth 10'. The spread of the inflammation through vascular channels of the aveolar bone 18 is shown by the arrows A and B in FIGS. 3 and 4. FIG. 3 illustrates an end view of two adjacent teeth 10A' having enamel 14'$_A$ and 10B' having enamel 14'$_B$ with the effects on the surrounding gum tissue 11, periodontal ligaments 13, and aveolar bone 18 due to the periodontal disease.

Oral biofilm communities begin to grow in the enlarged sulcus 24 of the periodontal tissues. First oral biofilm inhabitants are aerobic bacteria, but as the pocket 26 begins to develop, facultative bacteria biofilm begin to develop causing changes in the environment from an aerobic community to an oxygen depleted environment. This continues until the oxygen levels are obliterated resulting in the growth of obligate anaerobes that become the predominant biofilm species. The biofilm components, their products and the host products in response to the pathogenic community result in specific changes and alterations to the environment of the tooth and gums. These changes can include a breakdown of the host tissues, an inflammation of the gums, and a loss of tissue integrity, each of which further result in additional disease and infection.

In accordance with various embodiments of the present disclosure, an oxygenation or oxidation reduction medicament, antimicrobial or antibiotic or other medicament can be brought into repeated and direct contact with the biofilm community such that the medicament can penetrate the biofilm and alter the biofilm by chemical and/or mechanical means such that the biofilm community is affected. Furthermore, through continued use, any changes in the biofilm community can be maintained by repeated application of the medication to the micro-environment.

The destruction of the bony structure is caused by osteoclastic activity acid/base changes and other reasons. Although there is continuous osteoblastic activity, resulting in bone regeneration, but for various reasons the bone regeneration activity cannot keep up with the osteoclastic, bone destroying activity. In accordance with the present invention, when an antimicrobial medicament, such as a solution of tetracycline, is brought into repeated and direct contact with the diseased bone structure, usually below the gum line, it has surprisingly been found that the osteoblastic activity exceeds the osteoclastic activity resulting in net bone regeneration. In accordance with this invention, it has been determined that the tetracycline (or other medicament) solution slows osteoclastic activity but does not adversely affect osteoblastic activity. The bone regeneration decreases infection and body response to an infection and results in a marked decrease in the need for, and the invasiveness of, periodontal surgery.

In one embodiment, an apparatus such as a tray can be configured according to the present disclosure for the treatment of periodontal disease. Such an apparatus includes a body configured to be fitted about all of the upper or lower teeth of a patient for enclosing the teeth. The body can be monolayer made from an elastomeric material shaped to conform to the teeth and gums tissue proximate to the teeth of the patient.

In other embodiments, the body can be made to have a bilaminar structure with an outer wall and an inner wall composed of resilient elastomeric material molded for substantially conforming to enclosed teeth and gum tissue proximate to the teeth. The bilaminar body can have one or more internal recesses defined between the inner wall and the outer wall configured for receiving the enclosed teeth.

The body can be monolayer or bilaminar having a top outer surface positioned opposite to the one or more internal recesses and between an external surface of the outer wall and an external surface of the inner wall. A raised seal can be formed by the monolayer material or from bilaminar material such that it is formed about an inner surface of the outer wall and an inner surface of the inner wall and surrounding the recesses and corresponds to a location along a gum line of the patient associated with the enclosed teeth. The raised seal is configured to extend about the gum and spaced apart from the teeth, and to form a substantially air tight seal against the gum line.

A monolayer skirt is positioned external to the seal and a bilaminar skirt is positioned external to the outer wall and to the inner wall of the body having the raised seal formed thereon. The monolayer skirt or bilaminar skirt each have an outer portion configured to reinforce the outer wall and an inner portion configured to reinforce the inner wall, each reinforcement being proximate to the raised seal and each being configured to restrict an outward movement of the walls of the body during and after placement of the apparatus onto a portion of the gum tissue forming the gumline for increasing the substantial air tight seal against the gum tissue. The skirt can be formed as an extension of the body or the walls of the body, on an external surface. In some embodiments, the skirt can include an outer layer on the wall or incorporated into the wall for providing increased reinforcement to the wall and/or providing a resistive force to the wall to prevent or restrict the movement of the wall outward and thereby increasing the sealing force of the seal against the gumline when the tray assembly is fitted on a patient. This skirt/extension can be fortified in a monolayer thickness, or it can be bilaminar so a recess exists between the outer and inner surfaces of the seal.

FIGS. 5A-C to 9A-C are various embodiments of the skirt in exemplary relationship to the walls and the seals during the use of the tray and include exemplary structures and various features of such a tray assembly and its intended method of use for treatment of an oral biofilm.

Figures 5A, 5B, 5C:
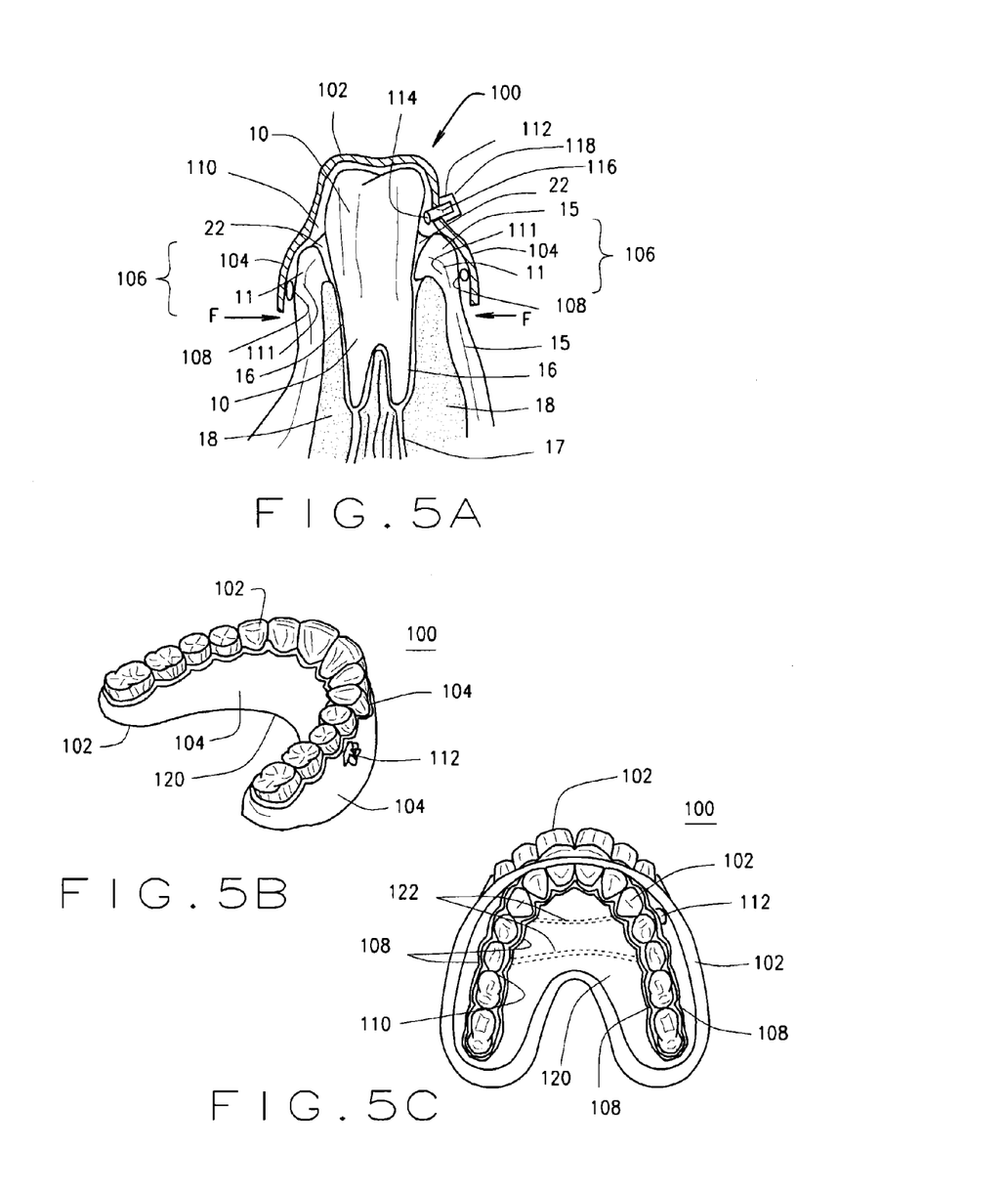
FIGS. 5A-5C are views of one exemplary embodiment of a positive pressure tray with FIG. 5A being a cross-sectional view of the positive pressure tray placed about a tooth and associated gum tissue, FIG. 5B being a top perspective view of the tray of FIG. 5A, and FIG. 5C being a bottom view of the tray of FIGS. 5A and 5B.

By way of example, FIGS. 5A-C illustrate a tray 100 having a body 102 with walls 104 also forming a skirt 106 and an air tight seal 108 positioned on an inner surface of the walls 104 forming a treatment chamber 110 or just chamber 110. The seal 108 is provided a biased contact in the direction of force arrow F with the surface of the gum tissue 11 or gingiva 15 by the skirt 106. The line of contact for the seal 108 with the gum tissue 11 around a set of teeth 10 is referred herein as gum line 111. Also shown for clarity in FIG. 5A is the nerve 17 of the tooth 10. In this embodiment, the skirt 106 portion of the walls 104 of the body 102 are composed of a reinforcing material for elastically resisting the outward movement of the walls 104 away from the tooth 10 and/or providing a bias force F of the seals 108 against the gum tissue 11 along the gum line.

In this exemplary embodiment, the skirt 106 can be a portion of the walls 104 or attached to the walls 104 with the skirt 106 being considerably less elastic resilience that of the upper portion of the body 102 of the tray 100. The walls 104 with the stiffened reinforcing skirt 106 in the area of the seal 108 working with the seal 108 biased against the gum line tissue 11, creates a chamber 110 between the tooth 10 and gum tissue 11 that encloses the CEJ 22 that can be pressurized. As shown, tray 100 can be contoured formed to fit an individual patient's teeth and can include a conforming of the seal 108 about each tooth 12 and continuously about all teeth 12.

After the tray 100 is placed about the tooth 10 (all teeth 10) the seal 108 provides an air tight enclosing of the chamber 110 about the teeth 10 and gum tissue 11 that includes the CEJ 22 and a pressure can be added to the chamber 110 through a pressure port 112. The amount of pressure will depend on the continuity and accuracy of the sealing of the seal 108 against the tissue of the gum line 111 as well at the amount of bias provided by the skirt 106 and/or walls 104 to the seal 108, as well as the integrity of the seal 108.

While a single pressure port 112 is shown, it is possible that more than one pressure port 112 or another embodiment of a pressure port 112 is provided. Generally, while not shown, one skilled in the art will understand from this disclosure that the pressure port 112 can include and orifice 114, a valve 116, an attachment fixture 118 with an attachment seal (not shown). A port value provides a passage from outside a wall 104 to the chamber 110 through which a fluid pressure (such as an air pressure, or pressurized medicament) from an external source is received. The pressure port can include a mating attachment for mating with a standard outside pressure source and a port seal that contains the pressure during the transfer and that will help to ensure the proper controlled receipt of the desired amount of pressure to the chamber 110.

In some embodiments, the body 102 of the tray 100 can include one or more conducting channels 122 the fluidly connect one or more regions of the chamber 110. The conducting channels 122 can enable the equalization of pressure throughout the chamber 110 and about the seal 108. The inclusion of conducting channels 122 can be included in a connecting portion 120 of body 102 as shown in FIGS. 5B and 5C with the conducting channels 122 traversing through the connecting portion 120 and fluidly connecting the two opposing inner side walls 104. In other embodiments, other arrangements are also possible. For example, in another embodiment the conducing channels 122 can be positioned laterally within a side wall 104 parallel to the seal 108, such as along the portion aligned with the gum line tissues 111 (also referred herein to as the gum line 111). Generally, the conducting channels 122 can include one or more orifices (not shown) that fluidly connect with the various portions of the chamber 110 for pressure equalization throughout the chamber 110.

In some embodiments, the monolayer skirt can be attached by or about a periphery to the outside surface of the walls external to the seal so as to form a skirt chamber between the skirt and the exterior wall that is substantially airtight. In such embodiments the skirt chamber can be prefilled with a variable stiffness material such as the herein described acrylic, by way of example, or it can include a port in the skirt. For example, filling composition can be placed within the skirt chamber during fabrication of the tray or can be later applied via the port. The port is fluidly coupled to the skirt chamber for selectively providing a filling composition into the skirt chamber. For example, the more filling composition added to the skirt chamber or positive pressure provided therein can increase the biasing force applied by the skirt to the wall and therefore to the seal against the gum line.

Figure 6A:
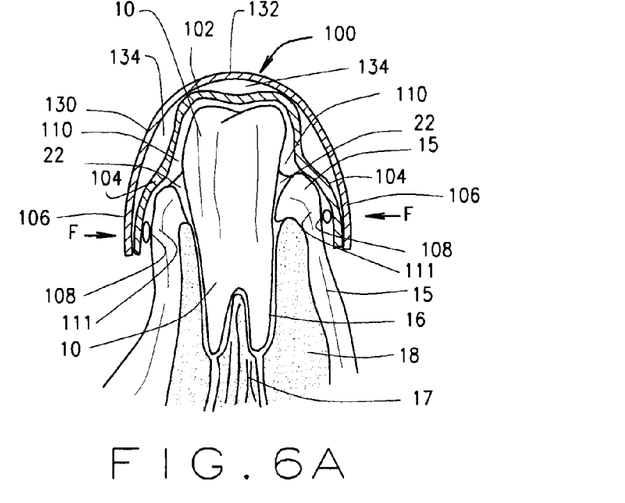
FIGS. 6A-6C are views of a second exemplary embodiment of a positive pressure tray with FIG. 6A being a cross-sectional view of the positive pressure tray placed about a tooth and associated gum tissue, FIG. 6B being a top perspective view of the tray of FIG. 6A, and FIG. 6C being a bottom view of the tray of FIGS. 6A and 6B.
Figures 6B, 6C:
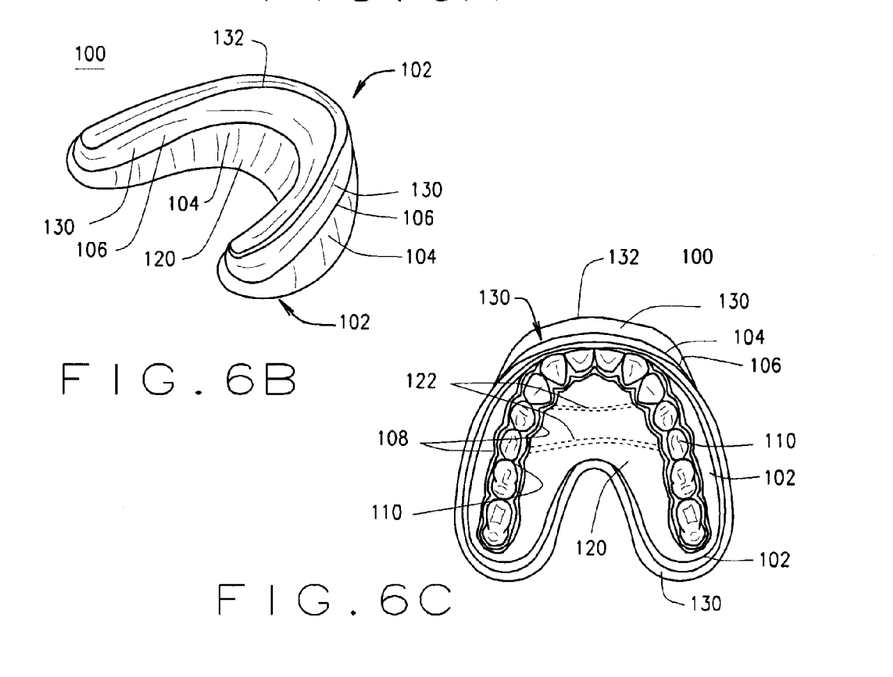

By way of example, FIGS. 6A-C are an embodiment of a skirt 106 being constructed to have a monolayer outer body 130 positioned outside of body 102 that forms the chamber 110 and includes the seals 108. In such embodiments, the skirt 106 that provides the biasing force F is a part of or formed by the monolayer outer body 130. In this manner, the body 102 forming the chamber 110 and having the seals 108 can be made of a consistent material, such as one ideally suited for forming to the contours of each patient's teeth and gum line. In some embodiments, the monolayer outer body 130 is formed as an external separate surface structure that can be attached or just placed over the body 102 before or after the body 102 is placed on the teeth 10 and gum tissue 11 to be treated. This could be referred to as a two-piece embodiment. In other embodiments, the monolayer outer body 130 can be attached or otherwise formed or constructed as a unibody with or on the external surfaces of the outer wall 104 of the body 102. In some embodiments, a skirt chamber 134 or ancillary chamber is formed between the outer body 130 and body 102 along one or more portions of the outer surface area of the body 102. The skirt chamber 134 may be filled or be a void.

The monolayer outer body 130 can be formed of an elastic resilient material and dimensioned to the walls 104 of the main body so that the skirt 106 of the monolayer outer body 130 can apply a pressure F to the wall 104 proximate to the seal 108. This can be preferably a consistent amount of pressure F along the length of the seal 108 and gum line 111

As shown the monolayer outer body 130 defines the skirt 106 having the inner skirt 106 outside of the inner wall 104 and the outer skirt 106 outside of the outer wall 104. The monolayer outer body 130 also includes a top connecting portion 132 connecting the two opposing skirts 106. The top connecting portion 132 can also add to the resilience and aid the skirts 106 in applying the biasing force F. As shown, the skirt 106 engages the outer surface of the outer and inner walls 104 defining the channel 110 therebetween to apply the biasing force F against each to restrict the outer movement of the walls 104 and/or to apply force F to each wall 104 and therefore to the outer and inner seals 108 along the gum line 111. The applied biasing force F of the skirt 106 of the monolayer outer body 130 increases the air tightness of the seal 108 against the gum line 111.

While not shown in FIGS. 6A-C, one or more pressure ports 112 as discussed above can be utilized with this embodiment as well. Such pressure ports 112 can penetrate and create a fluid connection from outside of the monolayer outer body 130 to inside the body 102 in connection with the chamber 110.

Figure 7A:
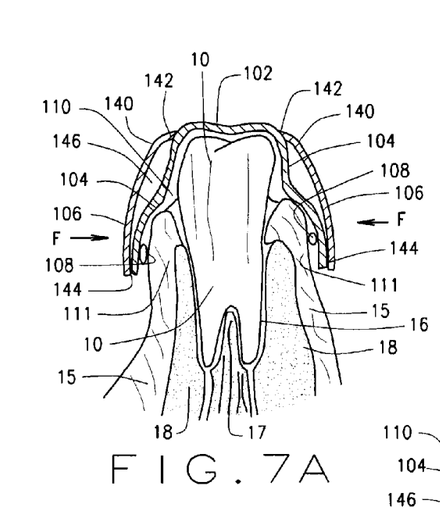
FIGS. 7A-7C are cross-sectional views of a third exemplary embodiment with the positive pressure tray placed about a tooth and associated gum tissue containing the biofilm wherein the top layer of the outer member is placed below the top of the tray and the bottom member is below the seal region (FIG. 7A), the bottom member is at the seal region (FIG. 7B), and the bottom member is above the seal region (FIG. 7C).
Figure 7B:
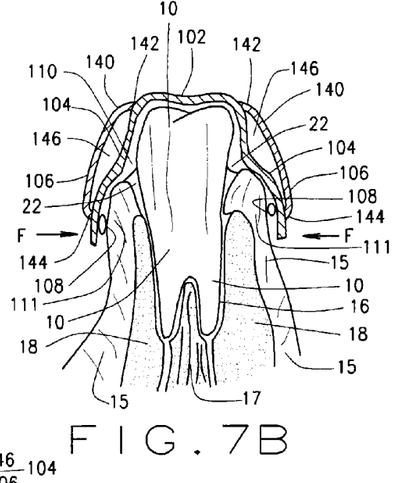
Figure 7C:
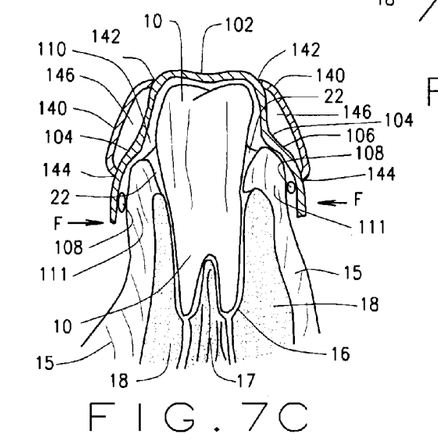

By way of another example, FIGS. 7A-7C are of another embodiment the positive pressure tray 100 can have the skirt 106 attached at one or more points on the outer surfaces of the walls 104 of the body 102 including the inside wall 104 and the outside wall 104. This embodiment differs from the embodiment of FIGS. 6A-6C as the skirt 106 is formed by outer layer 140 of wall 104 and does not include a full separate body 130 and does not include the top connecting portion 132. The outer layer 140 is composed of the resilient stiffened material for the skirt as described above.

The inner and outer skirts 106 of this embodiment are separate and not attached or connected and do not form a single unibody construction that covers the entire outer top surface of the body 102. As such, the outer layer 140 has an upper end 142 and a lower end 144, one or both of which can be attached to the body 102. In this embodiment, a skirt chamber 146 is formed between the outer surface of wall 104 and the inner surface of the skirt 106 which is formed by the outer layer 140. The skirt chamber 146 can be filled as described above or can be a void. The upper end 142 is attached to the wall 104 below a top of the body 102 of tray 100, but the position of such attachment can vary from that illustrated and still be within the scope of the present disclosure.

The orientation and position of the lower end 144 of skirt 106 can be different in slightly different embodiments. FIG. 7A illustrates a tray 100 having the lower end 144 of the skirt 106 or outer layer 140 position below or beyond the position of the seal 108 and/or the gum line 111. As shown, the lower end 144 can extend down the wall 104 to a point in close proximity to an end of the wall 104. The lower end 144 can be attached to the wall 104 at this point or the lower end 144 along with the other portions of the outer layer 140 can be formed with the body 102. In this embodiment, the lower end 144 of the skirt 106 exerts the biasing force F to the lower end of wall 104 and therefore biases or applies pressure to the seal 108 to the gum line 111.

In the embodiment of FIG. 7B, the tray 100 has the lower end 144 of skirt 106 is positioned proximate to or substantially with the seal 108, on the outside of wall 104 opposing the inner wall to which the seal 108 is attached or formed. The lower end 144 can be free or can be attached to the outer surface of wall 104 proximate an outer surface with the seal 108. In this embodiment, the lower end 144 of the skirt 106 exerts the biasing force 4 directly to the wall 104 on the other side of which is the seal 108 contacting the gum line 111. As such, the lower end 144 is providing a direct force F through the wall 104 to bias or pressure the seal 108 engagement with the gum line 111.

In the embodiment of FIG. 7C the lower end 144 of the skirt 106 is positioned above and/or away from a distal or free end of the wall 104 and above the position of the seal 108 in the direction of the upper end 142. The skirt 106 still applies the biasing force F to the wall 104 through the outer layer's attachment at the upper end 142 and its positioning at the lower end 144. The lower end 144 can be attached to the outer surface of wall 104 or can be free. In this embodiment, the resilience and stiffness of the skirt 106 from the upper end 142 through the outer layer 140 to the lower end 144 provides the biasing force F to the wall 104 and therefore to the seal 108 in the direction of the gum line 111.

Figure 8A:
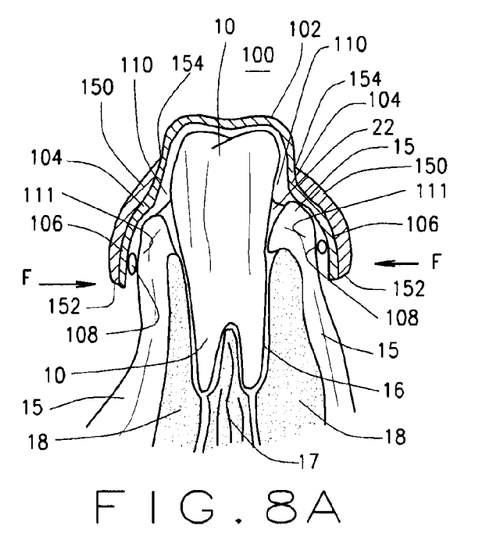
FIGS. 8A-8C are views of a fourth exemplary embodiment of a positive pressure tray with FIG. 8A being a cross-sectional view of the positive pressure tray placed about a tooth and associated gum tissue, FIG. 8B being a top perspective view of the tray of FIG. 8A, and FIG. 8C being a bottom view of the tray of FIGS. 8A and 8B.
Figures 8B, 8C:
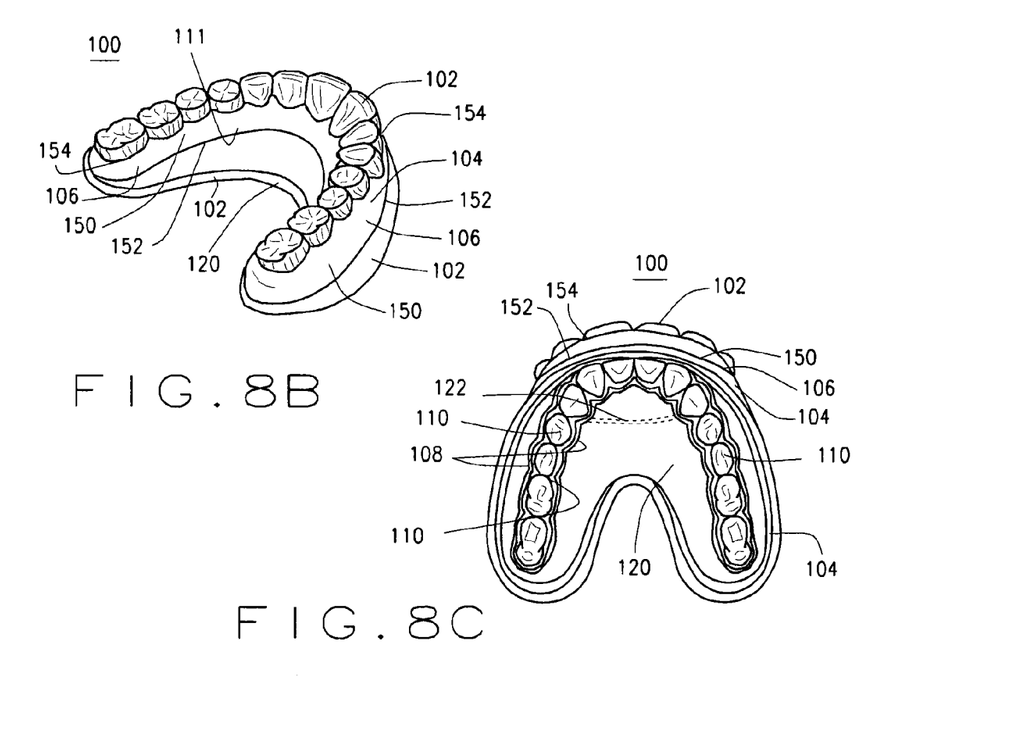

FIGS. 8A-C illustrate another embodiment that is similar to that of FIG. 7A-C, except in this embodiment, the skirt 106 has an outer layer 150 that is formed along or on the outer surface of the wall 104 of body 102 and does not create the skirt chamber. The outer layer 150 has a lower end 152 and an upper end 154 with the outer layer 150 being attached to the outer surface of the wall 104 from the upper end 154 to the lower end 152. Of course this attachment can be by way of co-forming or manufacturing. The skirt 106 formed on the outer surface of the wall 104 essentially creates a bilaminar formation, with the wall 104 being formed of one material and the outer layer 150 forming the skirt 106 being that of the described skirt material. In this embodiment, the outer layer 150 or skirt 106 provide the stiffness and biasing to the wall 104 and to the seal 108 towards to the gum line 111.

As noted above, in other embodiments, the skirt 106 can be a bilaminar structure defining a substantially airtight skirt chamber such as illustrated by ways of examples in the embodiments of FIGS. 9A-C and 10A-C.

Figure 9A:
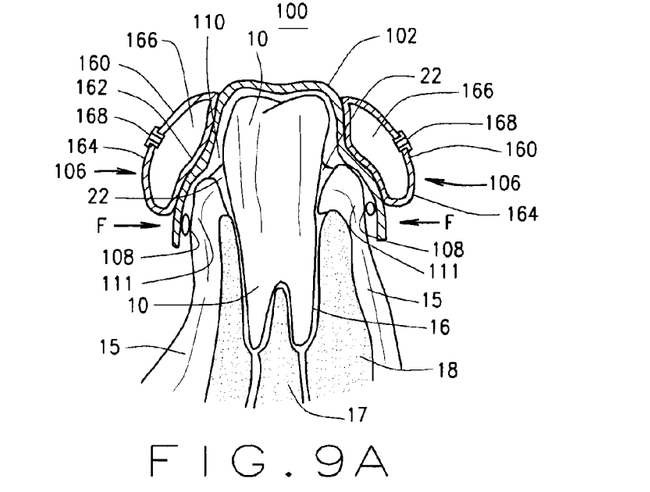
FIGS. 9A-9C are views of a fifth exemplary embodiment of a positive pressure tray with FIG. 9A being a cross-sectional view of the positive pressure tray placed about a tooth and associated gum tissue, FIG. 9B being a top perspective view of the tray of FIG. 9A, and FIG. 9C being a bottom view of the tray of FIGS. 9A and 9B.
Figures 9B, 9C:
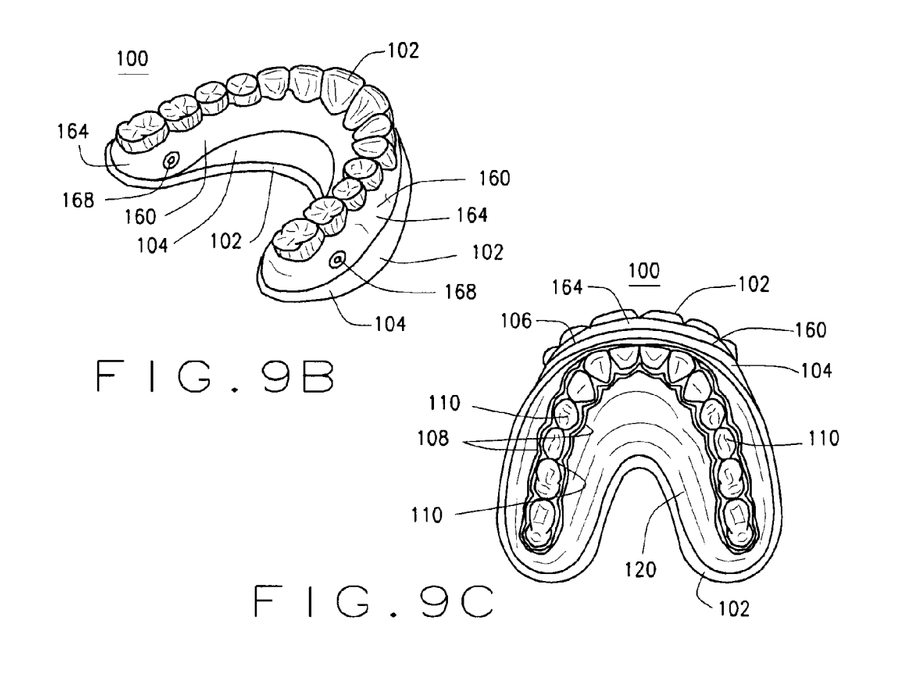

In the embodiment of FIGS. 9A-C, the skirt 106 is formed from a bilaminar structure 160 having a first layer 162 position on the outer surface of wall 104 and an opposing second layer 164 position opposite thereof, and forming an enclosed skirt chamber 166 therebetween. The skirt chamber 166 of the bilaminar structure 160 of this skirt 106 increases the reinforcement of the outer and inner wall 104 and provides an increase in biasing force F against the outer and inner walls 104 when the skirt chamber 166 is either fused with a filling material or receives a pressure from an external source. The skirt chamber 166 can be prefilled during fabrication of the tray 100 or post filled with a filling composition during use of the tray 100 with a patient. The bilaminar structure 160 of the skirt 106 can be attached about the outer surface of the outer and inner walls 104 for providing reinforcement thereto and in particular proximate to the portion of the walls 104 on which the seal 108 is positioned on the inner surface. The bilaminar structure 160 can provide for increasing biasing or applying an increased pressure or bias force F by placement of a positive pressure within skirt chamber 166 by way of one or more skirt ports 168. Additionally, an increased pressure result when the chamber 110 of the body 102 receives a treatment pressure.

The skirt port 168 is fluidly coupled to the skirt chamber 166 for receiving a filling composition or skirt pressure. This can include a filling composition such as a pressurized liquid, gas, or gel, such as an oxygenating source at a positive pressure, or can include a variable stiffness acrylic or other variable stiffness compound or composition. The skirt port 168 can include a valve (not shown) for selectively receiving the pressured liquid, gas, or gel and maintaining the received pressured filling composition for applying the biasing force F to the walls 104 and/or ensure that a desired pressure is maintained by the skirt chamber 166. A pressure limiter (not shown) can also be provided to ensure that no excessive pressure is provided to the skirt chamber 166.

Figure 10A:
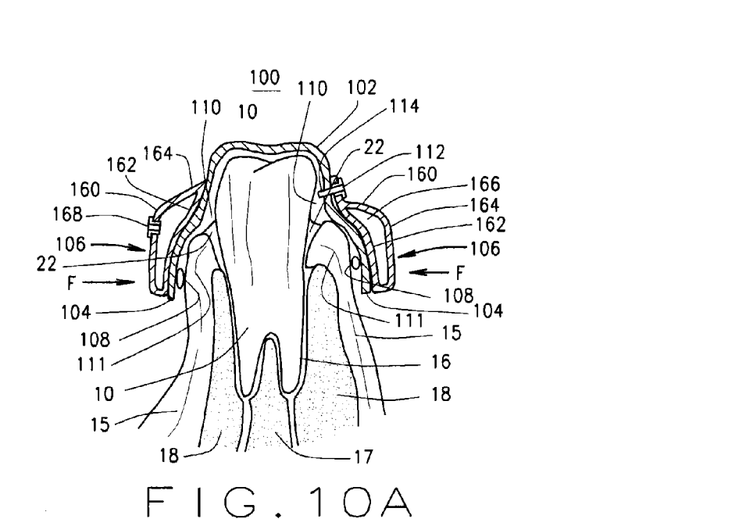
FIGS. 10A-10C are views of a sixth exemplary embodiment of a positive pressure tray with FIG. 10A being a cross-sectional view of the positive pressure tray placed about a tooth and associated gum tissue, FIG. 10B being a top perspective view of the tray of FIG. 10A, and FIG. 10C being a bottom view of the tray of FIGS. 10A and 10B.
Figures 10B, 10C:
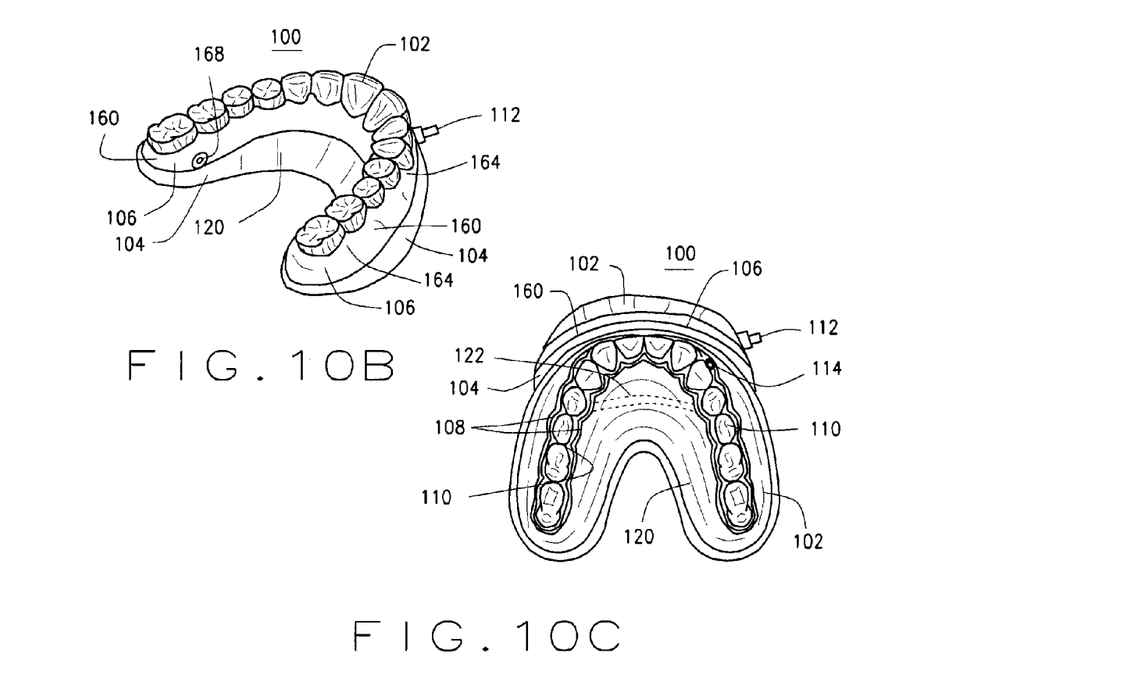

FIGS. 10A-C illustrates a slightly different bilaminar structure 160 that is lower on the wall 104 and proximate to the seal 108. In this illustrated embodiment, only a single skirt port 168 is illustrated. However, this also re-illustrates the inclusion of the pressure port 112 for receiving pressure into the treatment chamber 110 as described above. As noted, all of the embodiments, whether illustrated in the figures or not, may include one or more pressure ports 112.

As describe in these various exemplary embodiments, various materials could be incorporated into this body, the walls, the skirt and the seal to provide adequate pressure to maintain the contact with the gingiva to an airtight seal is maintained. Materials can be placed into the bilaminar recess by design during the fabrication of the tray, or a port can be fabricated into the design of the tray extension. The seal and the extension are configured to form a substantially air tight seal against all portions of the gum line.

In some embodiments at least a portion of one or more of these components can be partially or complete composed of an acrylic adapted for variable stiffness responsive to applied heat energy. A suitable acrylic is one that can be configured with the tray but also has a variable stiffness that can be adjusted by a caregiver to a desired stiffness during use by applying heat or electromagnetic energy, such as by hot or cold water or air, or by energy applied to filaments or other transducers placed within the acrylic or in close proximity thereto. For example, a variable stiffness acrylic can be used in the composition of the walls supporting the raised seal, in the skirt or as a filling compound within a skirt chamber. After the tray assembly is formed, the acrylic of the tray can be heated to allow for placement of the tray about the teeth and gums. The acrylic of the tray can then be cooled or allowed to cool wherein the acrylic stiffens and such stiffening increases biasing force of the seal about the gum tissue forming a portion of the gumline to increase the air tightness of such seal. This can also prevent the outward movement of the seal and/or wall of the tray during placement of a positive pressure within the treatment chamber also referred as the chamber. After the treatment is completed, the acrylic can once again be heated to allow for the removal of the biasing force and the removal of the tray from the teeth and gums.

Additionally, the body can include a port operatively coupled with one or more of the recesses forming the treatment chamber. The port has an external interface for coupling to a positive pressure source and/or a medicament source. This port provides for the selective placement of a positive pressure and/or medicament from an external source to within the treatment chamber. This can be a simple port for selectively allowing the placement of a medicament by way of the tip of a needle attached to a syringe, or can include an attachment mechanism or coupling means as may be suitable for attaching to a positive pressure and/or medicament source. The body port can be configured to receive a medication having a positive pressure and wherein the body, seal, skirt and port are configured for maintaining the received positive pressure about the enclosed teeth and gums.

The body port can include a valve for selectively receiving and maintaining a medication under positive pressure from a positive pressure medication source. For example, the body port can be configured for receiving a positively pressured oxygenating agent, such as hydrogen peroxide, from the positive pressure source. In such embodiments, the body, seal, skirt and port are configured for providing the received oxygenating agent within the recess and about the enclosed teeth and gum. This can also include, but is not limited to, coupling to an oxygenating, oxidative reduction, and/or ozone source or other gas, liquid or gel source or material.

In some embodiments, a pressure limiter can be provided in fluid connectivity to the medication chamber, or recesses or incorporated into the body for limiting an amount of positive pressure received into the recess from the positive pressure source. In this manner, the pressure limiter can be configured to prevent the receiving of a pressure that is harmful or that would tend to force the assembly/tray off of the substantially airtight seal with the gum tissue.

The body, seal, skirt and port are configured to cooperatively seal about the gum tissue forming a gumline and provide a medication chamber about the enclosed teeth and gums.

Additionally, in some embodiments, one or more conducting channels can be formed or provided in the body to fluidly connect two or more recesses together. In this manner, the conducting channels can equalize the pressure within the treatment chamber throughout the treatment chamber.

Additionally, in some embodiments, one or more electromagnet or energy conducting material such as an electrical or magnetic conducting material, by way of example, can be utilized in forming the body of the monolayer material or between the chambers of the bilaminar body. In this manner, the conducting material can provide a means of providing electrical, magnetic or other forms of energy within and throughout the treatment chamber. A means of external attachment to this conducting material can be provided via a port or other sealed attachment through the tray material.

According to one embodiment, a method for treating periodontal disease including fitting a tray about all of the upper or lower teeth of a patient. The tray has a body composed of resilient elastomeric material molded for substantially conforming to enclosed teeth and gum tissue proximate to the teeth. The body defines at least one recess to conform to the teeth. A raised seal surrounds the recess corresponding to a location along a gum line of the patient. The seal is configured to extend about the gum and spaced apart from the teeth. An extension is formed to support the seal and extend beyond the seal to engage the outer surface of the gum tissue. The extension of the tray material that extends over the gum tissue can be modified in thickness to provide adequate support to maintain an airtight seal around the teeth. This extension can be fortified in a monolayer thickness, or it can be bilaminar so a recess exists between the outer and inner surfaces of the seal. Various materials can be incorporated into this seal to provide adequate pressure to maintain the contact with the gingiva to as an airtight seal. Materials can be placed into the bilaminar recess by design during the fabrication of the tray, or a port can be fabricated into the design of the tray extension. The seal and the extension are configured to form a substantially air tight seal against all portions of the gum line. A port can be operatively coupled with the recess and has an external interface for coupling to a source of positive pressure so pressure of the extension can be altered to provide an airtight seal of the tray around the teeth. The body, seal and skirt/extension are configured to cooperatively seal about the teeth and gum tissue and to provide a positive pressure within the recess and about the teeth and gum tissue responsive and the extension contact and pressure generated against the tissue can be modified by receiving a positive pressure from the coupled positive pressure source or by receiving liquid, gel or other materials between the bilaminar portions of the seal extension. The method also includes applying a positive pressure within the tray to overcome crevicular flow so that an oxygenating agent, such as hydrogen peroxide, ozone or other oxidative/reductive materials can be applied to the gingival recess or periodontal pocket in the applied positive pressure within the recess and about the enclosed teeth and gums.

According to another embodiment, an apparatus for the treatment of periodontal disease including a body fitted to be about all of the upper or lower teeth of a patient. The body is composed of resilient elastomeric material molded for substantially conforming to enclosed teeth and gum tissue proximate to the teeth. In some embodiments, the body is composed of a material including impregnated fibers. Certain of these fibers may be used to conduct adequate electrical currents, or magnetic fields, or other forms of energy, that can activate or modify the medications placed within the tray and/or the micro-environment of the tissues enclosed or covered by the tray. Certain of these fibers can also be used to conduct light, magnet fields or other energy sources throughout the tray to activate, modify or in some manner alter the materials placed within the tray or the micro-environment of the material or tissues that are in close proximity or enclosed by the tray.

At least one recess is formed in the body to conform to the teeth. A raised seal surrounds the recess corresponding to a location along a gum line of the patient. The seal is configured to extend about the gum and spaced apart from the teeth and configured to form a substantially air tight seal against all portions of the gum line. An extension of the tray is formed to overlay the gum and oral tissues to complete the formation of the airtight seal, to support the seal and to serve to maintain an airtight environment. The seal can be monolayer, or bilaminar with a recess between the materials of the seal. A port is operatively coupled with the recess of the seal. The port has an external interface for coupling to a source of positive pressure or it can be configured to be a portal through which a syringe or other device can be introduced into the region between the outer and inner aspects of the seal so a liquid, gas, or gel could be introduced into this region. The body, seal and port are configured to cooperatively seal about the teeth and gum tissue and to provide a positive pressure within the recess and about the teeth and gum tissue responsive to provide a positive pressure from the coupled positive pressure source so an airtight association exists around the teeth and gums.

A body port can be configured through the tray material to reach the region around the teeth to receive a positively pressured oxygenating agent such as air, oxygen or other gas, hydrogen peroxide, ozone, oxidative reductive material or other agent from the positive pressure source. The body, seal and body port are then configured for providing a positively pressured oxygenating agent such as air, oxygen or other gas, hydrogen peroxide, ozone, oxidative reductive material or other agent within the recess and about the enclosed teeth and gum. The pressure can be modified in a manner that the external force can exceed the internal gingival crevice or periodontal pocket force so that materials can be delivered to the gingival crevice or periodontal pocket. As such, the external interface of the port can be configured for coupling to an oxygenating, ozone, oxidative/reductive source.

In some embodiments, the body includes one or more conducting channels connecting two or more sections of the recess for transmitting the received positive pressure and equalizing the positive pressure between the two or more sections of the recess.

In some embodiment a pressure valve can be coupled to the external interface of the port, the pressure valve configured for controlling the positive pressure received into the recess from the positive pressure source. In other embodiments, a pressure limiter is coupled to the external interface of the port for limiting the amount of positive pressure received into the recess.

In some embodiments, a skirt extends from the body and enclosing at least a portion of the seal. The skirt can be composed of a material having greater rigidity than the seal and configured for limiting the outward movement of the seal from the gum line. The skirt/extension can be monolayer or bilaminar in configuration. Materials can be placed between the bilaminar layers (gas, liquid, gel, other) to provide adequate pressure against the tooth surface and gum tissue to provide an airtight or adequate seal. The skirt can also have a port so that materials (liquid, gas, gel) could be selectively modified to increase or decrease the pressure of the tray skirt against the gum tissue, or the skirt can be modified in thickness and length of a monolayer material for pressure control.

As described herein, the present methods and systems can provide for the delivery of positive pressure based medications to a wound. In one embodiment, the positive pressure systems and methods provide for the positive pressure delivery of oxygen directly to the infected tissue positive pressure environment (hyperbaric oxygen) for the treatment of periodontal disease. Oxygen is bactericidal for anaerobic bacteria and possesses bacteriostatic effects and affects the growth and reproduction of some fungi and virus. The present disclosure discloses apparatus and methods whereby the use of local pressure can improve the medicinal effects of the oxygen as hyperbaric oxygen in improving wound healing and tissue repair. This can include increased collagen strength and the stimulation of new cell growth. The positive pressure application of oxygen can be in addition to any other doctor prescribed medications as oxygen can also enhances the function of antibiotics, increased neovascularization, promotes antigen and antibody function, is essential for new cell growth and promotes healing and there is very little negative reaction by prescribed medication. As provided herein, the localized application of oxygen under pressure provides for an alteration of the tissue environment from one conducive to disease to one conducive to health and healing. This environment of health and healing can be maintained by repeated application of the herein described tray and method through long-term use.

The pressurized direct delivery of oxygen to the infected area or wound can provide advantages that promote healthy recovery from an infection as the transcutaneous oxygen levels are increased, despite the lack of well vascularized wound tissue. These can include: a) acting as a catalyst for new healthy cell growth, promote the circulation of blood cells in infected tissue that has restrictions in the blood supply that occurs generally due to factors in the blood vessels that are in damaged or dysfunctional infected tissue, b) increasing the growth of new blood cells in the damaged tissue, c) increasing the flow of oxygenated blood to the wound to aid the healing process, d) fostering polymorphonuclear leukocyte and other infection agents functions, d) improving the vascularization of the new granulation tissue that is exposed to oxygen as the tissue heals, e) improving the tensile strength collagen being formed during wound healing, f) reducing scarring and the risk of recidivism, f) acting as a bactericidal for anaerobic bacteria present in the infected tissue (bacteriostatic effects on the biofilm). As the present methods and system provide for a new and improved topical treatment therapy, there is no systemic absorption of oxygen, and therefore no risk of pulmonary or central nervous system toxicity. Additionally, as provided herein a positive pressure oxygen therapy enhances macrophage activity, increases antibacterial effects, and increases antibiotic effects.

In one embodiment, a positive pressure delivery tray is configured to seals about the gums to provide a positive pressure environment (hyperbaric chamber) or treatment region within the chamber of the tray and about the enclosed teeth and gums including any infected areas. In some embodiments, a positive pressure delivery tray includes is configured with extensions and wall thickness that are bolstered to create a positive pressure within the tray and about the teeth, gums and the infected areas of the gums proximate to the teeth, such as periodontal pockets.

In some embodiments, positive pressure delivery tray can be made to include a positive pressure seal. Such positive pressure delivery tray seal can, in one embodiment, include a seal that is extended beyond the traditional dimensions of a medicament tray to provide a skirt that extends about and surrounds the seal. The skirt can be extended and thickened by a monolayer or bilaminar manner to provide rigidity for sealing about the gums to create the positive pressure within the treatment area within the chamber of the tray and about the enclosed teeth and gums. A port can be configured so that liquid, gel or gas can be inserted between the layers of the tray material to modify the pressure holding the tray and skirt material against the tooth and gum tissue.

Specific fibers can be incorporated into the tray material, seal and skirt to provide altered resiliency or to be able to conduct energy, magnetic changes or other means to enhance or modify the materials placed within the recesses of the tray which are delivered into the gingival crevice or periodontal pocket.

In another embodiment, positive pressure delivery tray can include a seal that is separately formed from the formation of a medicament delivery tray, but that is then bonded to the tray through an attachment process, such as by heat and pressure, or any other suitable attachment method.

The positive pressure tray can also be configured or formed from nontraditional medicament delivery tray materials. These new materials can include impregnated fibers or other materials as known to those skilled in the art after reading this disclosure that can add resiliency to the body of the positive pressure oxygenating tray, which may alter the energy fields within the tray, which may alter the magnetic fields within the tray or other modifications known to those skilled in these treatments. These can also be selected to provide the additional support to the overall structural integrity of the tray.

In some embodiments of the method and system, specialized appliances can be provided to provide a special bite relationship with a patient so that the trays are provided with a uniform contact upon closure of the mouth to be sure that the positive pressure that is provided within the treatment chamber is as equal as possible throughout the treatment chamber of the positive pressure tray. In this manner, the pressure is equal throughout the treatment chamber of the tray and the tray is not thrown off or a leak occurs due to variations in the pressure.

The positive pressure trays can provide the delivery of oxygen under pressure to the teeth and gums and in particular the infected gum tissue. The delivery of oxygen directly to the infected tissue can provide major tissue improvements. The positive pressure delivery tray can provide a product that generates oxygen, like ozone, or other oxidative/reduction materials directly about and to the infected area, e.g., the treatment area.

As described, in some embodiments a positive pressure delivery tray is configured with a body port for receiving oxygen or ozone, or other oxidative/reduction materials and retaining the doctor selected agent(s) directly about the infected gums. Of course, as one skilled in the art would understand, other embodiments can be provided that can similarly deliver the oxygenating agent to the infected gum and still be within the scope of the present disclosure.

The delivery of oxygen to the infected area or wound can provide advantages that promote healthy recovery from an infection. These can include acting as a catalyst for new healthy cell growth, promote the circulation of blood cells in infected tissue that has restrictions in the blood supply that occurs generally due to factors in the blood vessels that are in damaged or dysfunctional infected tissue, increases the growth of new blood cells in the damaged tissue, increases the flow of oxygenated blood to the wound to aid the healing process, fosters polymorphonuclear leukocyte and other infection agent functions, improve the vascularization of the new granulation tissue that is exposed to oxygen as the tissue heals, improves the tensile strength collagen being formed during wound healing, reduces scarring and the risk of recidivism, acts as a bactericidal for anaerobic bacteria present in the infected tissue and it has bacteriostatic effects on the biofilm. Of course, after reviewing the present disclosure, other advantages are also possible as would be recognized by those skilled in the art of wound management.

In one embodiment of such a method for treating periodontal disease one or more embodiments of the tray as described are fitted to a patient.

The method also includes applying a medicament within the recesses and creating a positive pressure within the recesses after the tray is fitted about the teeth and gums and about the medicament.

In another embodiment of a method for treating periodontal disease, a substantially airtight medicament tray is fitted to a patient. The tray defines a treatment chamber about the teeth and gum tissue of a patient to enclose the teeth and gum tissue. The fitted tray includes a raised seal for engaging gum tissue forming a gumline for forming a substantially airtight treatment chamber about the enclosed teeth and gum tissue. The method also includes inserting a medicament within the treatment chamber and applying a positive pressure to the substantially airtight treatment chamber and about the enclosed teeth and gum tissue.

The method can also include applying a biasing force to the seal against the gum tissue before or after or coincidental with the placement of the medicament within the recesses forming the treatment chamber. This can include engaging the skirt about the tray and proximate to the raised seal, injecting a positive pressure into a chamber of the tray, fitting the tray about the gum tissue with additional pressure, and applying energy to a portion of the tray to increase a stiffness of at least a portion of the tray.

One of the problems with prior systems and methods is that systemic oxygen delivery to the wound site is generally limited by poor wound tissue vascularization. However, topical hyperbaric oxygen as described herein can be delivered directly to the wound. As such, transcutaneous oxygen levels are increased, despite the lack of well vascularized wound tissue. As the present methods and system provide for a new and improved topical treatment therapy, there is no systemic absorption of oxygen, and therefore no risk of pulmonary or central nervous system toxicity. Additionally, as provided herein a positive pressure oxygen therapy enhances macrophage activity, increases antibacterial effects, and increases antibiotic effects.

When describing elements or features and/or embodiments thereof, the articles "a", "an", "the", and "said" are intended to mean that there are one or more of the elements or features. The terms "comprising", "including", and "having" are intended to be inclusive and mean that there may be additional elements or features beyond those specifically described.

Those skilled in the art will recognize that various changes can be made to the exemplary embodiments and implementations described above without departing from the scope of the disclosure. Accordingly, all matter contained in the above description or shown in the accompanying drawings should be interpreted as illustrative and not in a limiting sense.

It is further to be understood that the processes or steps described herein are not to be construed as necessarily requiring their performance in the particular order discussed or illustrated. It is also to be understood that additional or alternative processes or steps may be employed.

What is claimed is:

1. An apparatus for the treatment of an oral biofilm associated with periodontal disease comprising:
    a body configured to be fitted about all of the upper or lower teeth of a patient for enclosing the teeth, the body having walls that include an outer wall and an inner wall, each composed of resilient elastomeric material molded for substantially conforming to the enclosed teeth and gum tissue proximate to the teeth, one or more internal recesses defined between the inner wall and the outer wall and configured for receiving the enclosed teeth, and having a top outer surface positioned opposite to the one or more internal recesses and between an external surface of the outer wall and an external surface of the inner wall;
    a raised seal formed about an inner surface of the outer wall and an inner surface of the inner wall and surrounding the one or more recesses and corresponding to a location along a gum line of the gum tissue of the patient associated with the enclosed teeth, the raised seal being configured to extend about the gum tissue and spaced apart from the teeth, and configured to form a substantially air tight seal against the gum line; and
    a skirt positioned external to the outer wall and to the inner wall of the body having the raised seal formed thereon, the skirt reinforcing the outer wall and the inner wall and providing increased stiffness with respect to the body and a biasing force thereto and to the raised seal to the gum line after placement of the apparatus onto the gum tissue and about the teeth,
    wherein the skirt is composed as a bilaminar structure with a substantially airtight skirt chamber, the skirt increasing the reinforcement of the outer and inner walls and providing an increased biasing force against the outer and inner walls when the skirt chamber is filled with a filling composition and
    wherein the skirt chamber is filled with an acrylic adapted for variable stiffness responsive to applied heat energy.

2. The apparatus of claim 1 wherein the skirt is composed of a material having substantially less elastic resilience than a material forming the body.

3. The apparatus of claim 1 wherein the skirt engages the outer surface of the outer and inner walls and to apply a biasing force against thereto in addition to restricting the outer movement of the walls, and the skirt applies a biasing force in the direction of the seal towards the gum tissue of the gum line.

4. The apparatus of claim 1 wherein the body includes two or more recesses and wherein the body further includes one or more conducting channels connecting the two or more recesses for fluidly coupling each of the two or more recessing recesses together.

5. The apparatus of claim 1 wherein the body includes at least a portion of electromagnet conducting material adapted for conducting externally applied energy through the body and about the treatment chamber.

6. The apparatus of claim 5 wherein the body includes impregnated fibers for conducting externally applied magnetic or electrical energy through the body.

7. The apparatus of claim 1 wherein the walls of the body are at least partially composed of an acrylic adapted for variable stiffness during use of the apparatus responsive to applied heat energy as applied during use of the apparatus.

8. The apparatus of claim 1 wherein the body and recess are configured for receiving a medicament consisting of an oxygenating agent, an oxygen/reduction agent, and ozone, and wherein the medicament is applied or creates a positive pressure within the recess and about the enclosed teeth and gums.

9. The apparatus of claim 1 wherein the raised seal conforms about each enclosed tooth and is continuous about all enclosed teeth.

10. The apparatus of claim 1 wherein the skirt includes two skirt portions, an inner skirt portion and an outer skirt portion, the inner skirt portion positioned external to the inner wall of the body and providing the biasing force against an inner gum line on a first side of the enclosed teeth and the outer skirt portion positioned external to the outer wall of the body and providing the biasing force against an outer gum line on an opposing second side of the enclosed teeth.

11. The apparatus of claim 10 wherein the two skirts are separate and not attached or connected together and do not form a single unibody construction.

12. The apparatus of claim 1 wherein the raised seal sealing against the gum line is configured to form the substantially air tight seal by the seal being biased with the biasing force along the contact of the seal with the enclosed gums.

13. The apparatus of claim 1 wherein the skirt has an upper end fixedly attaching the skirt to the walls of the body enclosing the teeth and gums, the skirt chamber having an upper end defined by the fixed attachment of the skirt to the walls and a lower end extending downward therefrom to a lower point of attachment of the skirt to the walls.

14. The apparatus of claim 13 wherein the lower end extends downward to a point in close proximity to a lower end of the walls of the body, and wherein the raised seal is formed spaced apart from the lower end of the walls.

15. The apparatus of claim 13 wherein the raised seal is formed spaced apart from a lower end of the walls and the lower end of the skirt extends downward to a position the walls that is on the opposing side of the walls from the raised seal.

16. The apparatus of claim 13 wherein the raised seal is formed spaced apart from a lower end of the walls and the lower end of the skirt extends downward to a position above the position of the raised seal.

17. The apparatus of claim 13 wherein the lower end of the skirt is a free end that is not attached to the walls of the body and contacts the wall and provides the biasing force against the wall at a point of contact therewith.

18. The apparatus of claim 1 wherein the skirt is attached by a periphery to the outside surface of the walls and forms a skirt chamber between the skirt and the wall that is substantially airtight.

19. The apparatus of claim 1 wherein the skirt defines the skirt chamber as a void between an upper end of the skirt, which is attached to an upper portion of one of the outer wall and the inner wall, and a lower end of the skirt, which is disposed downward in a direction toward a free end of wall to which it is attached.

20. The apparatus of claim 1 wherein the skirt defines the skirt chamber between an upper end of the skirt that is attached to an upper portion of at least one of the outer wall and the inner wall and a lower end of the skirt that exerts a biasing force against an external lower portion of the wall to which the skirt is attached for providing the biasing force to the raised seal and against the gum line.

* * * * *